US006238674B1

(12) United States Patent
Renimel et al.

(10) Patent No.: US 6,238,674 B1
(45) Date of Patent: May 29, 2001

(54) USE OF AN EXTRACT OF *CORDIA DICHOTOMA*

(75) Inventors: Isabelle Renimel, Trainou; Marc Olivier, Les Angles; Patrice Andre, Neuville aux Bois; Pierre Cabalion, Noumea, all of (FR)

(73) Assignee: Parfums Christian Dior, Paris (FR)

( * ) Notice: Subject to any disclaimer, the term of this patent is extended or adjusted under 35 U.S.C. 154(b) by 0 days.

(21) Appl. No.: 09/319,935

(22) PCT Filed: Dec. 18, 1997

(86) PCT No.: PCT/FR97/02343

§ 371 Date: Jun. 18, 1999

§ 102(e) Date: Jun. 18, 1999

(87) PCT Pub. No.: WO98/27957

PCT Pub. Date: Jul. 2, 1998

(30) Foreign Application Priority Data

Dec. 20, 1996 (FR) .................................................. 96 15794

(51) Int. Cl.$^7$ ........................... A61K 35/78; A61K 6/00; A61K 7/00; A61K 7/42

(52) U.S. Cl. ........................ 424/195.1; 424/59; 424/401; 514/844; 514/887

(58) Field of Search ................................. 424/195.1, 401, 424/59; 514/844, 887

(56) References Cited

U.S. PATENT DOCUMENTS 4,554,170 * 11/1985 Panzner et al. ...................... 426/651

FOREIGN PATENT DOCUMENTS

8208498 * 8/1996 (JP) .

OTHER PUBLICATIONS

Choudhary et al. Indian J. Exp. Biol., vol. 28 (8), pp. 714–716, abstract enclosed, 1990.*
Masood et al. Indian Forester, vol. 111 (10), pp. 841–845, 1985.*

* cited by examiner

*Primary Examiner*—Christopher R. Tate
(74) *Attorney, Agent, or Firm*—Dennison, Scheiner, Schultz & Wakeman

(57) ABSTRACT

A method of treating a human body for delaying effects of ageing on skin thereof, by applying to a part of the skin in need thereof of a cosmetic or pharmaceutical composition containing an amount of an extract of *Cordia dichotoma* effective to inhibit activity of elastase in the skin, obtaining thereby the delaying of the effects of ageing on the skin.

11 Claims, No Drawings

USE OF AN EXTRACT OF *CORDIA DICHOTOMA*

BACKGROUND OF THE INVENTION

The invention relates to uses of an extract of the plant *Cordia dichotoma* in the cosmetic and pharmaceutical fields, especially the dermatological field.

The plant *Cordia dichotoma* belongs to the Boraginaceae family which is found particularly in New Caledonia.

This plant is well known in traditional Polynesian medicine for its uses as an anti-inflammatory.

Cataplasms in particular are prepared from this plant.

The emollient properties of this plant are equally as well known as its asepsis properties.

SUMMARY OF THE INVENTION

The inventors of the present application have now discovered that the extracts of this plant furthermore present excellent anti-elastic properties, which allows for their use as active principle in cosmetic or pharmaceutical, especially dermatological, compositions intended to combat all effects linked to the ageing of the skin.

More precisely, the invention is the result of systematic experiments carried out by the inventors with a view to studying the enzymatic reactions of extracts of *Cordia dichotoma*.

These systematic experiments have revealed a certain activity of these extracts on elastase.

More precisely, the systematic experiments carried out by the inventors are concerned with the following enzymes: elastase, tyrosinase and 3',5'-cAMP phosphodiesterase.

DETAILED DESCRIPTION OF THE INVENTION

Elastase, elastin degradation enzyme, is present in the cells, especially in the dermal cells (fibroblasts) just as, in a smaller measure, in the epidermal cells (keratinocytes). It has been observed that the quantity and activity of elastase increases during the cutaneous ageing process, intrinsic as well as actinic. By a degradation of the elastin fibres, the result of the elastase action is a loss of cutaneous elasticity, a relaxing of the skin and the appearance of wrinkles.

3',5'-cAMP phosphodiesterase, hereafter called "phosphodiesterase" or "PDE", is the enzyme which converts cAMP, a second messenger involved in controlling cell metabolism, to inactive AMP. Consequently, the inhibition of PDE by an inhibitor makes it possible to maintain a high intracellular level of cAMP, which has the effect especially of activating the protein kinases A and, via this process, makes it possible to promote lipid degradation.

Furthermore, it is also known that cAMP plays a part in counteracting certain inflammatory processes (Hitchcock M., J. Immunol (1977) 188 557). Also it has been described that phosphodiesterase increases with age (Puri S. K. and Volicer L., Mechanisms of Ageing and Dev. (1981) 15 239. The inhibition of phosphodiesterase will therefore make a contribution to combating the effects of ageing, particularly on the skin.

Tyrosinase is the key enzyme in the synthesis of melanin and hence in the metabolism of skin pigmentation. In cosmetics, the inhibition of tyrosinase by appropriate agents has applications in the local treatment of skin hyperpigmentations such as senescent pigmentary marks.

These tests have shown the very clear activity of extracts of the plant *Cordia dichotoma* on the inhibition of elastase, and have led the inventors of the present invention to preparing cosmetic or dermatological compositions useful in any application aimed at combating ageing of the skin. Thus, according to one of its essential characteristics, the invention relates to the use of an extract of the plant *Cordia dichotoma* as active principle of a cosmetic composition intended to combat the effects of ageing on the skin, especially by preserving or improving the biomechanical properties of the skin, particularly its elasticity, by delaying the appearance of wrinkles or by reducing their depth, and by improving the firmness of the skin.

According to another essential characteristic of the invention, it also relates to the use of an extract of the plant *Cordia dichotoma* for the preparation of a pharmaceutical, especially dermatological, composition intended for the treatment of intrinsic or actinic ageing effects on the skin, said extract being incorporated in a pharmaceutically acceptable vehicle.

In the two fields of cosmetic and dermatological application, it is essentially the leaves which are found to be of value in the preparation of the extracts of the invention.

The extract is advantageously obtained by maceration of the plant or part of the plant in a polar solvent or polar solvent mixture, followed by filtration. The solvent of the solution obtained can be evaporated off, if necessary, to give the dry extract.

The evaporation will preferably be performed under reduced pressure.

The following may be mentioned as solvents which are advantageously used:
  water
  $C_1$ to $C_6$ alcohols such as methanol, ethanol and isopropanol
  $C_2$ to $C_6$ polyols such as propylene glycol or glycerol, and mixtures thereof.

Water is found to be a particularly useful extraction solvent.

The plant extract could also be obtained by the so-called supercritical carbon dioxide extraction technique.

In one advantageous embodiment, this composition comprises 0.001% to 10% by weight and particularly 0.02% to 1% by weight of dry plant extract, based on the total weight of the final composition.

Furthermore, the experiments carried out by the inventors have clearly shown that not only the extraction yield but also the enzymatic activity of the extract is related to the nature of the solvent used. The attached Examples clearly show the effect of the choice of solvent on the enzymatic activity of the extract.

The cosmetic or pharmaceutical compositions according to the invention can be formulated in any form acceptable for their use in cosmetology or in pharmacy, especially in dermatology. Particularly, the composition can be in a form appropriate for topical application, specifically in the form of a cream or gel and particularly a cream or gel for the face, hands, bust or body.

According to another aspect, the invention relates to the use of the plant extract as a cosmetic agent, said agent being incorporated in a cosmetic composition as defined above.

This cosmetic agent will be used especially in all applications which are aimed particularly at inhibiting the action of elastase.

The cosmetic compositions according to the invention will also be used to combat the effects of skin ageing, especially by preserving or improving the biomechanical properties of the skin, particularly its elasticity, by delaying the appearance of wrinkles or reducing their depth and by improving the firmness of the skin.

Thus, according to another aspect, the invention relates to cosmetic compositions intended for skin care and particularly for combating the effects of skin ageing.

As mentioned above, it has been possible to correlate the efficacy of the cosmetic compositions as well as the above described dermatological compositions with the anti-elastic activity of the extract.

In all the applications, the compositions used are preferably compositions for topical application which are intended for application to the skin.

The Examples which follow are given purely in order to illustrate the invention.

Unless indicated otherwise, the proportions given in the Examples of compositions are expressed as percentages by weight.

EXAMPLE 1

Preparation of an Aqueous Extract According to the Invention 1g of leaves of the plant *Cordia dichotoma*, dried and ground beforehand, were introduced into 200 ml of water. The suspension was left to stand at room temperature for 4 hours, with moderate stirring. The mixture was subsequently filtered and the solvent was then evaporated off from the resulting filtrate under reduced pressure. The dry extract was then recovered. Compositions of the invention can be prepared either by using the dry extract or by using an optionally concentrated solution of plant extract in the extraction solvent.

EXAMPLE 2

Study of the Inhibitory Activity of the Extracts on Different Enzymes 2.1 Extracts Used As the enzymatic inhibition tests were performed in aqueous media, it was necessary to use water-miscible extraction solvents.

Thus, by following the procedure described in Example 1, three different extracts were prepared with water, methanol and DMSO respectively. The concentration of these extracts was then adjusted to 0.5% of dry plant extract, either by addition or by evaporation of the extraction solvent.

All the tests described below were carried out in triplicate. The values reported are arithmetic means.

2.2 Inhibition of Elastase a) Principle of the Test:

The techniques for demonstrating the inhibition of elastase have been described by various authors (J. S. Baumstark, et al., Biochim. Biophys. Acta (1963), 77 676; Bieth, B. et al., Biochem. Med., (1974), 11, 350; Franck C., Byrjalsen I., Biol. Chem. Hoppe Seyler, (1988) 369 (8) 677–82).

The active principle was as follows: a substrate was brought into contact with elastase in an aqueous medium and then, after incubation, the reaction products were measured.

In the present case the substrate was N-succinyl-(Ala)$_3$-paranitroaniline, available from Sigma (ref.: S4760), in a solution containing 0.5 mg/ml in 0.2 M Tris-HCl buffer of pH 8.8. The elastase added to the reaction medium released the paranitroaniline and the peptide residue. The course of the reaction was observed on a Uvikon 941® spectrophotometer (Kontron S.A.) at a wavelength λ of 379 nm.

The composition of the reaction medium was as follows:

| | |
|---|---|
| substrate solution (0.5 mg/ml of buffer): | 200 µl |
| Tris-HCl buffer: | 600 µl |
| extraction solvent: | 100 µl |

The extraction solvent either did or did not contain the effector, i.e. the extract of the plant *Cordia dichotoma* at a concentration of 0.5% by weight, depending on whether a test with effector or a test without effector (baseline activity of the enzyme) was being carried out.

100 µl of the enzyme solution, containing 35 U/ml in the Tris-HCl buffer, was added to these 900 µl of reaction medium immediately before use.

The kinetics of release of paranitroaniline were then measured by the absorption of monochromatic light of wavelength 379 nm on a spectrophotometer, enabling the percentage inhibition $I_E$ to be calculated according to the following formula:

$$I_E = \frac{\Delta AbB/\min - \Delta AbE/\min}{\Delta AbB/\min} \times 100$$

in which ΔAbB/mn is the difference in absorbance per minute of the reaction medium for the baseline activity and ΔAbE/min is the difference in absorbance of the reaction medium for the test with effector. The absorbance values considered were those corresponding to the linear period of the change in absorbance as a function of time.

The results are shown in Table I below.

2.3 Inhibition of Phosphodiesterase (PDE).

The principle of this test was based on the hydrolysis of cyclic 3',5'-adenosine monophosphate (cAMP) to adenosine monophosphate (AMP). The formation of AMP was measured by HPLC analysis.

The composition of the reaction medium is indicated below. The solutions of the reagents were prepared in 0.05 M Tris-HCl buffer of pH 7.5.

| | |
|---|---|
| solution of cAMP (substrate) at 0.25% in the buffer | 80 µl |
| solvent, without or with effector at 0.5% | 80 µl |
| Tris-HCl buffer | 480 µl |

160 µl of PDE, at a concentration of 0.5 U/ml in the Tris-HCl buffer, were added to this medium immediately before use.

At time t=5 minutes, the quantity of AMP formed was measured by calculating the surface area of integration of the AMP peak on the chromatogram produced by the HPLC apparatus (KONTRON S.A.).

The level of inhibition IA of PDE by the effector can then be estimated according to the following formula:

$$I_A = \frac{SAMP_b - SAMP_e}{SAMP_b} \times 100$$

in which $SAMP_b$ represents the surface area of integration of the AMP peak for the baseline activity of the enzyme (without effector) and $SAMP_e$ represents the surface area of integration of the AMP peak for the activity of the enzyme in the presence of the effector.

The results obtained are shown in Table I below.

2.4. Inhibition of Tyrosinase

The principle of this test was based on the formation of dopachrome from L-tyrosine by the action of tyrosinase.

It is pointed out that, in the presence of tyrosinase and oxygen, L-tyrosine oxidizes to L-DOPA, which in turn oxidizes to dopaquinone, again through the action of tyrosinase. Dopaquinone then cyclizes to cyclodopa, which oxidizes to dopachrome; this is a precursor of melanins and absorbs light at a wavelength of 480 nm.

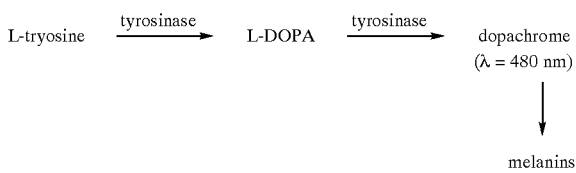

The formation of dopachrome can therefore be followed by spectrophotometry.

For this method, particular reference may be made to the publications by Pomerantz S. H., Arch. Biochem. Biophys. (1974) 160 73–82, or Barber J., J. Invest. Dermatol. (1984) 83 145–149.

The composition of the reaction medium is indicated below. The solutions of the reagents were prepared in 0.02 M phosphate buffer of pH 6.9.

| | |
|---|---|
| solution of L-tyrosine (1st substrate) at 1 mM in the buffer | 333 μl |
| solution of L-DOPA (2nd substrate) at 1 mM in the buffer | 333 μl |
| solvent, without or with effector at 0.5% | 333 μl |

33 μl of tyrosinase solution, at a concentration of 2400 U/ml in the phosphate buffer, were added to this reaction medium immediately before use.

The kinetics of formation of dopachrome were then measured by the absorption of monochromatic light of wavelength 480 nm on a Uvikon 941 spectrophotometer (KONTRON S.A.), making it possible to calculate, for the linear part of the change in absorbance as a function of time, the percentage inhibition IT of tyrosinase according to the following formula:

$$I_T = \frac{\Delta AbB/\min - \Delta AbE/\min}{\Delta AbB/\min} \times 100$$

in which ΔAbB/min is the difference in absorbance per minute of the reaction medium for the baseline activity of the enzyme (without effector) and ΔAbE/min is the difference in absorbance of the reaction medium for the test with effector.

The results are shown in Table I below.

TABLE I

Level of enzymatic inhibition by the extracts of the invention

| | Extract | | |
|---|---|---|---|
| | $E_{water}$ | $E_{methanol}$ | $E_{DMSO}$ |
| $I_E$ (elastase) | 96 | 1 | 14 |
| $I_T$ (tyrosinase) | 1 | — | — |
| $I_A$ (PDE) | 2 | 1 | 2 |

$E_{water}$: 0.5% aqueous extract
$E_{methanol}$: 0.5% methanol extract
$E_{DMSO}$: 0.5% DMSO extract The results shown in Table I above demonstrate the value of the extracts according to the invention in the cosmetic and pharmaceutical fields, especially the dermatological field, wherever the action of certain enzymes is to be blocked, reduced in magnitude or regulated.

More precisely, it is clearly apparent that the action of the aqueous extract of *Cordia dichotoma* is particularly signifi-cant on the inhibition of elastase. However, this extract is not active on the inhibition of tyrosinase or phosphodiesterase. The methanolic and DMSO extracts of this plant do not seem to have any inhibitory effect on the other enzymes tested.

Therefore, the extracts of *Cordia dichotoma*, particularly the aqueous extracts, can advantageously be used for the different applications mentioned above which follow from the inhibition of elastase, such as cutaneous firming and combating the ageing effects on the skin, such as the appearance of wrinkles.

EXAMPLE 3

Cosmetic Anti-Wrinkle Gel

| | |
|---|---|
| Dry extract of Example 1, | 0.05 g |
| Carbomer | 0.3 g |
| Glycerol | 3.0 g |
| Tetrasodium EDTA | 0.05 g |
| Aqueous extract of witch hazel | 3.00 g |
| Polymethyl methacrylate | 1.00 g |
| Perfumes, preservatives, color, neutralizer | qs |
| Distilled water | qsp 100 g |

This gel has a soothing anti-wrinkle effect.

EXAMPLE 4

Anti-Wrinkle Cream for the Face

| | |
|---|---|
| Dry extract according to Example 1, | 0.5 g |
| Glyceryl stearate + PEG 100 stearate | 5.0 g |
| Cetyl alcohol | 1.0 g |
| Stearyl alcohol | 1.0 g |
| Beeswax | 1.50 g |
| Squalane | 3.0 g |
| Hydrogenated polyisobutene | 4.0 g |
| Cetearyl octanoate | 1.50 g |
| Glycerol tricaprylate/caprate | 3.0 g |
| Dimethicone | 1.0 g |
| Xanthan gum | 0.2 g |
| Carbomer | 0.15 g |
| Glycerol | 2.0 g |
| Neutralizer, preservative, perfumes, colors | qs |
| Water | qsp 100 g |

EXAMPLE 5

Cream for Sensitive Skin

| | |
|---|---|
| Dry extract of Cordia dichotoma leaves, prepared according to Example 1 | 0.2 g |
| Methyl glucose sesquistearate | 3.0 g |
| Beeswax | 3.0 g |
| Behenyl alcohol | 3.0 g |
| Octyl octanoate | 5.0 g |
| Fluid mineral oil | 7.5 g |
| Cetostearyl octanoate | 5.0 g |
| Glycerol | 3.0 g |
| Xanthan gum | 0.50 g |
| Perfumes | 0.30 g |
| Preservative, colors | qs |
| Water | qsp 100 g |

This cream is used to firm the skin on the face and neck.

What is claimed is:

1. A method of treating a human body for delaying effects of ageing on skin thereof, comprising applying to a part of the skin in need thereof of a cosmetic or pharmaceutical composition containing an amount of an extract of *Cordia*

*dichotoma* leaves obtained by extraction with at least one polar solvent effective to inhibit activity of elastase in the skin, obtaining thereby said delaying of the effects of ageing on the skin.

2. The method according to claim 1, wherein said composition contains an amount of said extract effective to preserve or improve biomechanical properties of the skin, by delaying the appearance of wrinkles or by reducing their depth, and by improving the firmness of the skin.

3. The method according to claim 1, wherein said composition contains an amount of said extract effective to improve elasticity of the skin.

4. The method according to claim 1, additionally comprising obtaining said extract by maceration of *Cordia dichotoma* leaves in at least one polar solvent, followed by filtration and, optionally, evaporation of the at least one solvent.

5. The method according to claim 4, wherein said solvent is selected from the group consisting of water, $C_1$ to $C_6$ alcohols, $C_2$ to $C_6$ polyols and mixtures thereof.

6. The method according to claim 5, wherein said solvent is water.

7. The method according to claim 1, additionally comprising obtaining said extract by supercritical carbon dioxide extraction.

8. The method according to claim 1, wherein said composition comprises from 0.001% to 10% by weight of dry extract of *Cordia dichotoma*.

9. The method according to claim 1, wherein said composition is formulated for topical application.

10. The method according to claim 1, wherein the polar solvent is selected from the group consisting of water, $C_1$ to $C_6$ alcohols, and $C_2$ to $C_6$ polyols.

11. The method according to claim 1, wherein the at least one polar solvent comprises water and at least one additional polar solvent.

* * * * *